United States Patent [19]

Omura et al.

[11] Patent Number: 5,336,783
[45] Date of Patent: Aug. 9, 1994

[54] CALPAIN INHIBITOR CYSTAMIDIN A AND ITS PRODUCTION

[75] Inventors: Satoshi Omura; Haruo Tanaka; Kazuro Shiomi, all of Tokyo, Japan; Jing R. Liu, Beijing, China

[73] Assignee: The Kitasato Institute, Tokyo, Japan

[21] Appl. No.: 57,731

[22] Filed: Mar. 23, 1993

[30] Foreign Application Priority Data

Apr. 20, 1992 [JP] Japan .................. 4-099666
Feb. 5, 1993 [JP] Japan .................. 5-019001

[51] Int. Cl.⁵ .................. C07D 207/323
[52] U.S. Cl. .................. 548/561
[58] Field of Search .................. 548/561

[56] References Cited

U.S. PATENT DOCUMENTS 4,376,778  3/1983  Ezaki et al. .................. 548/557
5,075,452  12/1991  Kirchlechner et al. .................. 548/561

FOREIGN PATENT DOCUMENTS 3-157366  7/1991  Japan .................. 548/557
4-095069  3/1992  Japan .................. 548/557

OTHER PUBLICATIONS

"Darstellung von histaminahnlichen Substanze aus der pyrrolreihe", Hoppe-Seyler's Zeitschrift fur Physiologische Chemie, Band 289, Heft 1, 1952, By Kutscher et al., pp. 229–233.

"The Role of Concepts in Structure–Activity Relationship Studies of Opioid", *Journal of Medicinal Chemistry*, vol. 35, No. 11, 1992, By P. Portoghese, pp. 2047–2054.

*Primary Examiner*—Mary C. Lee
*Assistant Examiner*—Joseph K. McKane
*Attorney, Agent, or Firm*—Young & Thompson

[57] ABSTRACT

A novel calpain inhibitory active and low molecular weight substance, cystamidin A and its production are provided. Cystamidin A of the following formula

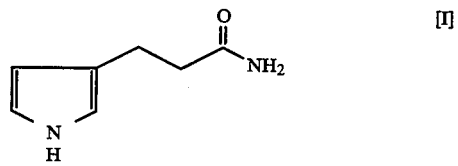

was produced by culturing Streptomyces sp. KP-1241 FERM BP-41 71 in a nutrient medium and isolating the active substance from the cultured mass.

2 Claims, 4 Drawing Sheets

CALPAIN INHIBITOR CYSTAMIDIN A AND ITS PRODUCTION

FIELD OF THE INVENTION

This invention relates to a novel calpain inhibitor, cystamidin A, and to a process for its production.

PRIOR ART

Calpain is a calcium-dependent cysteine protease which occurs in various kinds of mammalian tissues. The enzyme is presumed to play a central role in physiological or pathological events, and to be involved in the activation of kinase-series enzymes such as protein kinase C and phosphorylase kinase B by limiting proteolysis, and in the decomposition of cytoskeletal proteins and of growth-factor- and hormone-receptors. Diseases related to calpain are known. It is strongly suggested to be involved in the turnover of muscle in muscular dystrophy, for example, and in the disappearance of the Z line in skeletal muscle (Experimental Medicine, 5:942 (1987)).

Furthermore, in a cell infected with human T-cell leukemia virus, extremely increased activities of calpain and interleukin 2 receptor are observed. This may be caused by an irregular reaction of cells to growth factor due to alteration of receptor activity by an action of calpain on cytoskeletal protein (Biochemistry, 57:1202 (1985)). Still further, calpain is thought to have a relation to myocardial infarction (Experimental Medicine, 5:937 (1987)), demyelination (Modern Medicine, 43:81 3 (1988)) and inflammation (ibid., 43:776 (1988)).

Calpastatin which is a specific inhibitory protein as to calpain, is known, and is expected to be applicable as an effective therapeutic agent for various excessive calpain-related syndromes. Calpastatin is, however, a high molecular weight protein and hence it will be difficult to use as a medicine. A low molecular weight calpain inhibitor is therefore desirable.

OBJECT OF THE INVENTION

An object of the present invention is therefore to provide a novel low molecular weight calpain inhibitor and a process for its production.

SUMMARY OF THE INVENTION

It has now been found that a strain belonging to the genus Streptomyces produces calpain inhibition in its cultured broth.

An object of the present invention is therefore to provide a novel low molecular weight calpain inhibitor and a process for its production.

It has also been found that this calpain inhibition is due to a novel compound cystamidin A of the formula

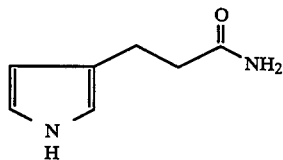

[I]

The invention also provides a process for the production of cystamidin A, which comprises culturing a cystamidin A-producing microorganism belonging to the genus Streptomyces, and isolating the thus-produced cystamidin A from the cultured mass.

DETAILED DESCRIPTION OF THE INVENTION

Figure 1:
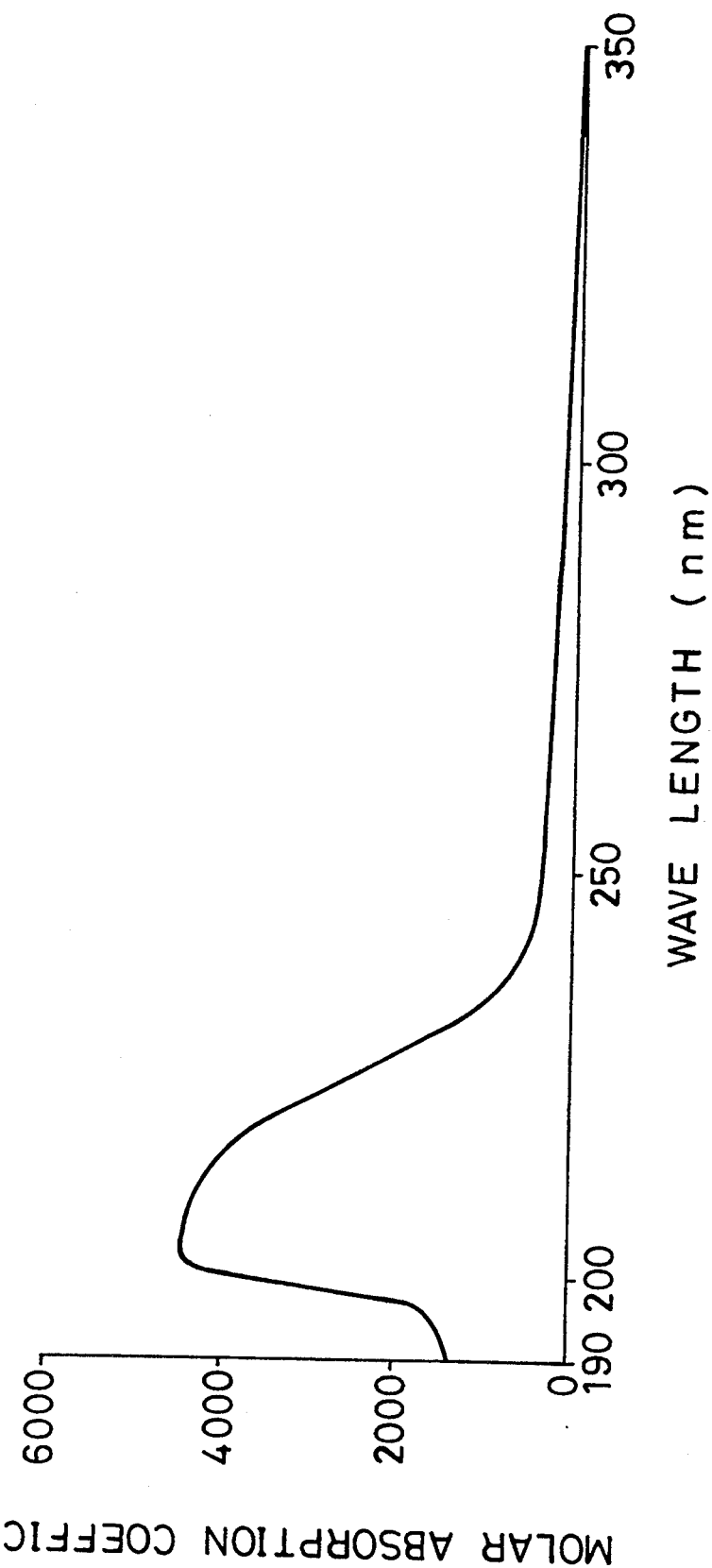
FIG. 1: UV spectrum of cystamidin A.

Cystamidin A of the present invention can be produced by culturing a cystamidin A-producing microorganism belonging to the genus Streptomyces in a nutrient medium, accumulating the cystamidin A in the medium, and isolating the calpain inhibitor cystamidin A therefrom. The cystamidin A-producing microorganism can be a cystamidin A-producing microorganism of the genus Streptomyces and is not limited to the strain disclosed in this specification. A preferred example of cystamidin A-producing microorganism is Streptomyces sp. KP-1241 isolated from a soil sample collected in China by the present inventors. The taxonomical properties of the strain KP-1241 are set forth hereinbelow.

1. Morphological properties

The vegetative mycelia grow abundantly on both synthetic and complex agar media and do not show fragmentation into coccoid forms or bacillary elements. The aerial mycelia grow abundantly on inorganic salts-starch agar and glycerol-asparagine agar to show a grayish color. The mature sporophores form spiral spore chains and have more than 20 spores per chain. The spores are oval in shape, 1.0 μm×0.7 μm in size and have a spiny surface. Whorls, sclerotic granules, sporangia and flagellated spores are not observed.

2. Cultural characteristics

The cultural characteristics are shown in Table 1. To investigate the cultural characteristics and physiological properties of the strain, the International Streptomyces Project (ISP) medium recommended by Shirling and Gottlieb (*Int. J. Syst. Bacteriol.*, 16:313–340 (1966)) was used. Color Harmony Manual, 4th Ed., 1958 (Container Corporation of America, Chicago) was used for color names and hue numbers. Cultures were observed after incubation at 27° C. for two weeks, if not otherwise specified.

TABLE 1

| Cultural Characteristics of Strain KP-1241 | |
|---|---|
| Medium | Cultural Characteristics |
| Sucrose-nitrate agar | G: poor, colorless |
| | R: silver gray (3fe) |
| | AM: poor, silver gray (3fe) |
| | SP: none |
| Glucose-asparagine agar (ISP) | G: good, light ivory (2ca) |
| | R: light wheat (2ea) |
| | AM: abundant, silver gray (3fe) |
| | SP: none |
| Glycerol-asparagine agar (ISP) | G: good, colorless |
| | R: bamboo (2gc) |
| | AM: abundant, silver gray (3fe) |
| | SP: none |
| Inorganic salts-starch agar (ISP) | G: good, light ivory (2ca) |
| | R: covert tan (2ge) |
| | AM: abundant, dark covert gray (2ih) |
| | SP: none |
| Tyrosine agar (ISP) | G: moderate, light ivory (2ca) |
| | R: pale pink (3ca) |
| | AM: poor, white (a) |

TABLE 1-continued
Cultural Characteristics of Strain KP-1241

| Medium | Cultural Characteristics |
|---|---|
| Oatmeal agar (ISP) | SP: poor<br>G: moderate, colorless<br>R: silver gray (3fe)<br>AM: moderate, beige gray (3ih) |
| Yeast extract-malt extract agar (ISP) | SP: none<br>G: good, colorless<br>R: mustard (21e)<br>AM: abundant, dark covert gray (2ih) |
| Nutrient agar | SP: none<br>G: good, colorless<br>R: bisque (3ec)<br>AM: moderate, white (a) |
| Peptone-yeast extract iron agar (ISP) | SP: none<br>G: moderate, light ivory (2ca)<br>R: honey gold (2ic)<br>AM: moderate, white (a) |
| Glucose-nitrate agar | SP: none<br>G: moderate, light mustard tan (2ie)<br>R: mustard (21e)<br>AM: poor, white (a) |
| Glycerol-calcium malate agar | SP: none<br>G: good, light ivory (2ca)<br>R: light ivory (2ca)<br>AM: poor, white (a) |
| Glucose-peptone | SP: none<br>G: moderate, bamboo (2gc)<br>R: bisque (3ec)<br>AM: moderate, white (a)<br>SP: amber (3pe) |

Abbreviations:
G: growth of vegetative mycelium
R: reverse
AM: aerial mycelium
SP: soluble pigment
ISP: International Streptomyces Project 3. Physiological Properties (+ =active; — =inactive)

| | | |
|---|---|---|
| (1) | Melanin formation | |
| | (a) Tyrosine agar | + |
| | (b) Peptone-yeast extract iron agar | + |
| | (c) Glucose-peptone-gelatin medium (21-23° C.) | — |
| | (d) Tryptone-yeast liq. | — |
| (2) | Tyrosinase reaction | + |
| (3) | $H_2S$ production | — |
| (4) | Nitrate reduction | + |
| (5) | Liquefaction of gelatin (21-23° C.) | + |
| (6) | Hydrolysis of starch | + |
| (7) | Coagulation of milk (27° C.) | — |
| (8) | Peptonization of milk (27° C.) | + |
| (9) | Temperature range for growth 12-34° C.<br>Optimum temperature range for growth 24° C. | |
| (10) | Utilization of carbon sources<br>(Pridham and Gottlieb agar medium)<br>Utilized: D-glucose, D-mannitol, D-fructose, i-Inositol;<br>Weakly utilized: L-arabinose, D-rhamnose;<br>Not utilized: D-xylose, raffinose, melibiose, sucrose. | |
| (11) | Cellulolytic activity | |

4. Chemical composition

The DAP (diaminopimelic acid)-isomer in the cell wall of strain KP-1241 is determined to be LL-type.

The taxonomical properties of the strain KP-1241 are illustratively summarized as follows. The DAP-isomer in the cell wall is LL-type. The aerial mycelia form spiral spore chains with smooth surfaces. As to the cultural characteristics, the vegetative mycelia show white or gray on various media. Soluble pigment is slightly produced in tyrosine agar and glucose-peptone agar.

From the taxonomic properties described above, strain KP-1241 is considered to be the white or gray series of the genus Streptomyces according to the classification by Pridham and Tresner (*Bergey's Manual of Determinative Bacteriology*, Vol. 8, pp. 748-829, 1974). The strain is referred to as genus Streptomyces and the species is designated Streptomyces sp. KP-1241. The strain was deposited in the National Institute of Bioscience and Human Technology, Agency of Industrial Science and Technology, Japan, under the name Streptomyces sp. KP-1241 and the accession No. is FERM BP-41 71.

In the present invention, the above strain is merely illustrative, and the above strain, its mutants and other cystamidin A-producing microorganisms belonging to the genus Streptomyces can naturally be used. The calpain inhibitor, cystamidin A of the present invention can be produced by inoculating and culturing aerobically the above strain, for example, in a nutrient medium suitable for cystamidin A production. A nutrient source such as any nutrient medium for Streptomyces can be used.

Commercially available nitrogen sources such as peptone, meat extract, corn steep liquor, cotton seed meal, peanut meal, soybean meal, yeast extract, NZ-amine, casein hydrolyzate, sodium nitrate, ammonium nitrate and ammonium sulfate, and carbon sources such as glycerin, starch, glucose, galactose, lactose and mannose can be used. Furthermore, carbon sources such as fatty substances, and inorganic salts such as sodium chloride, phosphate salts, calcium carbonate and magnesium sulfate can also be used.

The other essential trace metallic salt and anti-foam agents such as animal, vegetable or mineral oil can be added to the medium if required. These nutrient sources and other additives useful for the production of cystamidin A can be used, which is to say that any cultural material for Streptomyces can be used in the present invention. Liquid culture such as submerged aeration culture is preferable for quantity production of cystamidin A. The temperature for culturing the microorganisms can be adjusted to grow the strain within a range of suitable production of cystamidin A. Culturing conditions can be selected and controlled for the production of cystamidin A, depending upon the nature of the production microorganisms.

Cystamidin A is mainly produced in a cultured broth. Crude cystamidin A can be isolated by extracting the cultured filtrate with a water-immiscible organic solvent such as butanol, or by eluting the absorbed substance in an absorption resin with a water-containing organic solvent. In addition to the above extraction procedure, the isolation method used for low molecular weight substances such as absorption chromatography, gel-filtration chromatography, preparative thin layer chromatography, countercurrent partition chromatography and high performance liquid chromatography, and preferably combinations and repetitions thereof, can be used for isolating and obtaining pure cystamidin A.

Figure 2:
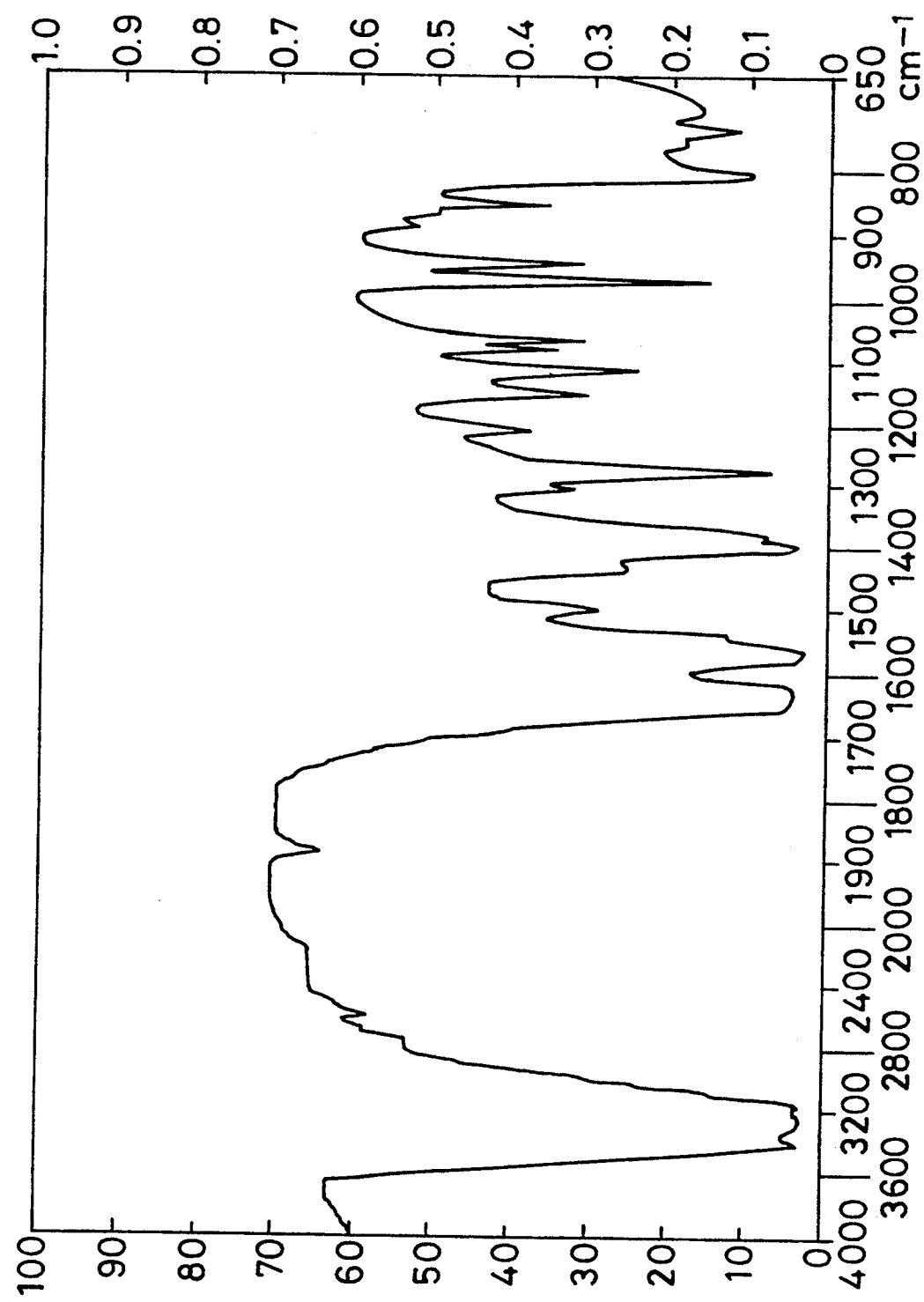
FIG. 2: IR spectrum of cystamidin A.
Figure 3:
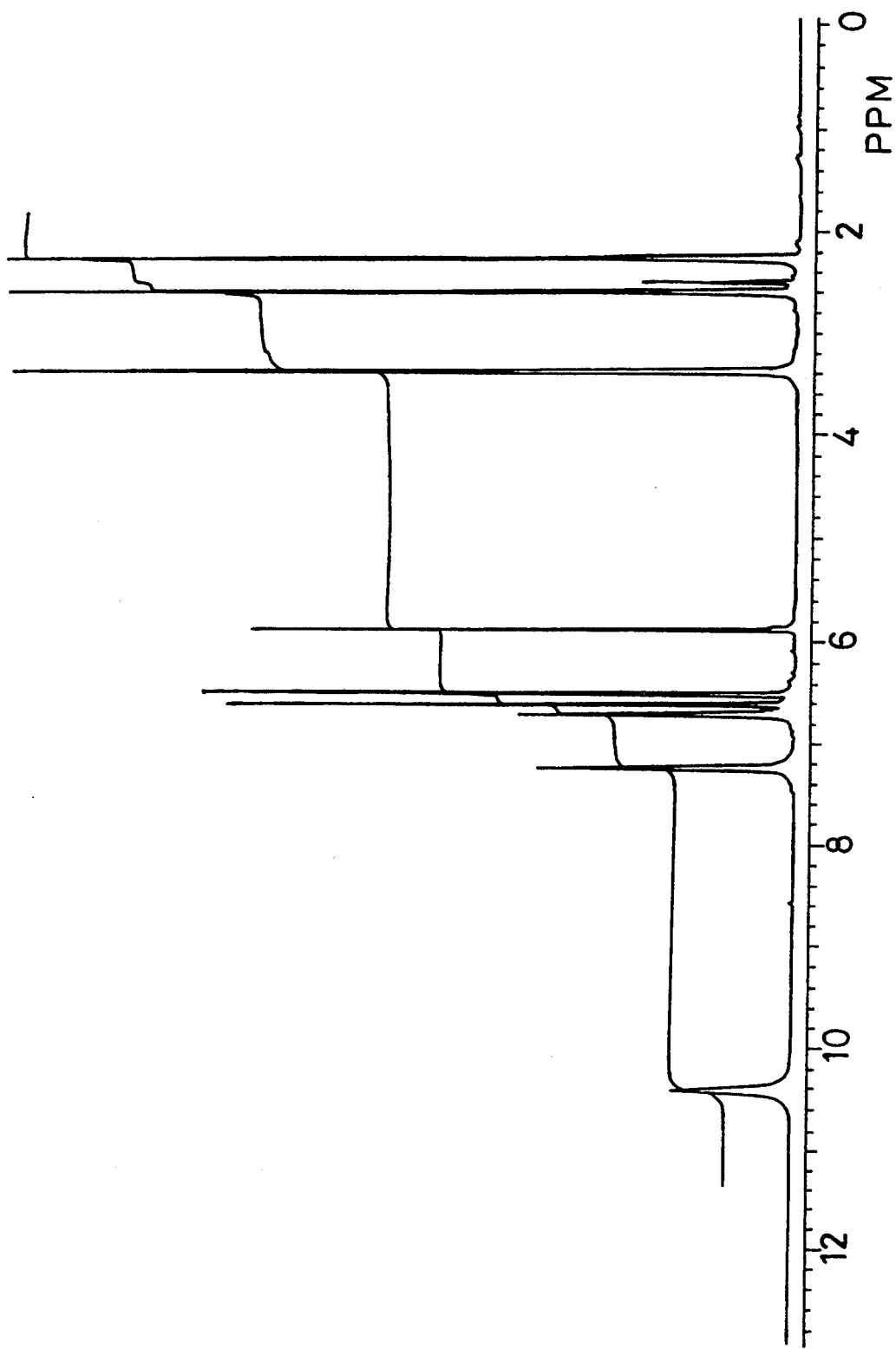
FIG. 3: $^1$H-NMR spectrum of cystamidin A.
Figure 4:
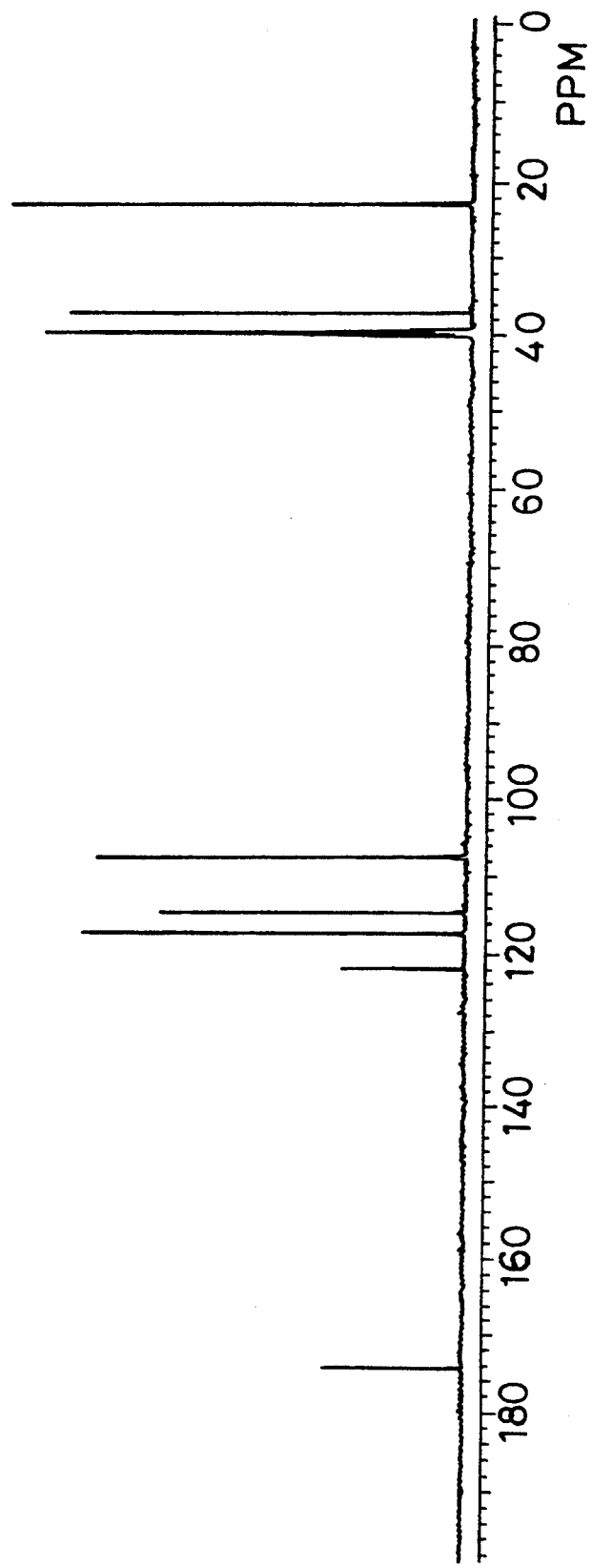
FIG. 4: $^{13}$C-NMR spectrum of cystamidin A.

The physico-chemical properties of cystamidin A are shown by the following:
1. Nature: white powder
2. Molecular weight: 138.0793 (by mass spectrometric analysis)
3. Molecular formula: $C_7H_{10}N_2O$ 4. Melting point: 146°–148° C.
5. Ultraviolet absorption maximum (in methanol): (FIG. 1) 203 nm ($\epsilon=4400$), 213 nm (shoulder, $\epsilon=4100$), 260–280 nm (shoulder, $\epsilon=300$)
6. Infrared absorption maximum (KBr tablet): (FIG. 2) 3400, 3250, 3150, 1640, 1570, 1400, 1280, 1110, 970, 805, 740 cm$^{-1}$
7. $^1$H-NMR spectrum (in DMSO-d$_6$, ppm): (FIG. 3) 10.40 br. s (1H), 7.24 br. s (1H), 6.69 br. s (1H), 6.60 dd (1H), 6.50 dd (1H), 5.86 dd (1H), 2.59 t (2H), 2.25 t (2H)ppm (s=singlet, d=doublet, t=triplet, br=broad)
8. $^{13}$C-NMR spectrum (in DMSO-d$_6$, ppm): (FIG. 4) 174.3 s, 121.8 s, 117.3 d, 114.6 d, 107.5 d, 37.0 t, 22.8 t
9. Solubility in solvent: soluble in water, methanol, acetone, chloroform and benzene
10. Color reaction: positive for ninhydrin, Ebrlich and Rydon-Smith reagents From the above physico-chemical properties and the spectra data, the structure of cystamidin A was elucidated as shown in the formula (1) hereinbefore.

As illustrated in detail by the physico-chemical properties of cystamidin A, the substance has never been known and reported and is a novel compound.

The biological properties of cystamidin A are illustrated as follows:

The inhibitory activity of cystamidin A against calpain using casein as substrate according to the method by Saito et al. (*Agr. Biol. Chem.*, 51:361 (1987)), IC$_{50}$ (50% inhibition) is 0.20 µg/ml.

Cystamidin A shows no antimicrobial activity at 100 µg/disk (paper disk method) against various kinds of bacteria, yeast and fungi. The IC$_{50}$ value against B-16 melanoma cells in vitro was more than 25 µg/ml. The LD$_{50}$ (ip) of cystamidin A in mice is >200 mg/kg.

Effect of the Invention

As explained hereinabove, the novel compound cystamidin A is a low molecular weight substance and shows strong inhibitory action on calpain. Therefore it can be used not only as a reagent but also as a pharmaceutical.

EXAMPLES

The present invention will be illustrated by the following examples, which are, however, not to be construed as limiting.

EXAMPLE 1

A loopful of mycelia of a stock culture of Streptomyces sp. KP-1241 FERM BP-4171 was transferred into each of 14 flasks each of which was a 500-ml Erlenmeyer flask containing 100 ml of a medium consisting of glucose 0.1%, soluble starch (Kanto Chem. Co.) 2.4%, peptone (Kyokuto Pharmaceutical Industrial Co.) 0.3%, meat extract (Kyokuto Pharmaceutical Industrial Co.) 0.3%, yeast extract (Oriental Yeast Co.) 0.5% and CaCO$_3$ 0.4% (pH 7.0 before sterilization), and the mixture was then incubated on a rotary shaker at 27° C. for 3 days to give a seed culture. The seed culture (1.4 lit.) was inoculated into a tank fermenter containing 70 liters of a medium consisting of glycerol 2.0%, soybean meal 2.0% and NaCl 1 0.3% (pH 7.0 before sterilization), and the medium was incubated with agitation at 200 rpm and aeration at the rate of 35 lit./min. at 27° C. for 4 days.

The cultured broth was centrifuged and the supernatant was charged on a column of Diaion HP20 (5 lit., Mitsubishi Chem. Ind. Ltd.) and eluted with 20% methanol. The eluate (25 lit.) showing calpain inhibitory activity was extracted twice with ethyl acetate (18 lit.) The extract was concentrated in vacuo to obtain a brownish oil (55 g). This oil was dissolved in water (1.5 lit.), introduced onto a reversed phase silica gel column (1000 ml, YMC* GEL ODS-AQ 120-S50, YMC Co.) packed with 50% methanol, and developed with 20% methanol.

The active fractions were collected and concentrated in vacuo to obtain another brownish oil (7.2 g). The latter oil was dissolved in a small volume of methanol, and the solution was mixed with silica gel powder (50 g, Merck Art. 7734), then methanol was stripped from the mixture under reduced pressure. The dried silica gel was introduced onto a column of silica gel (210 g, Merck Art. 7734) and eluted with a mixture of chloroform and methanol (30:1). The active fraction was collected and evaporated under reduced pressure to give still another brownish oil (439 mg).

The last oil was dissolved in a small volume of methanol and applied on HPLC (Capcell Pak C18, SG120, $\phi$20 ×250 mm, Shiseido Co.) separately 12 times, with 5% acetonitrile at a flow rate of 8 ml/min., checking and detecting the absorption at 205 nm. The peak showing calpain inhibitory activity, eluted for 17 min., was collected. The extract was concentrated under reduced pressure to obtain a white powder of cystamidin A (370 mg).

What is claimed is:
1. Cystamidin A of the formula

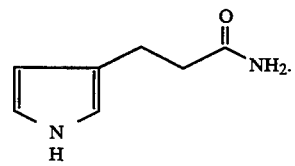

2. Cystamidin A which has the following physico-chemical properties:
   (1) Nature: white powder
   (2) Molecular weight: 138.0793 (by mass spectrometric analysis)
   (3) Molecular formula: C$_7$H$_{10}$N$_2$O
   (4) Melting point: 146°–148° C.
   (5) Ultraviolet absorption maximum (in methanol): 203 nm ($\epsilon=4400$), 213 nm (shoulder, $\epsilon=4100$), 260–280 nm (shoulder, $\epsilon=300$)
   (6) Infrared absorption maximum (KBr tablet): 3400, 3250, 3150, 1640, 1570, 1400, 1280, 1110, 970, 805, 740 cm$^{-1}$
   (7) Solubility in solvent: soluble in water, methanol, acetone, chloroform and benzene
   (8) Color reaction: positive for ninhydrin, Ebrlich and Rydon-Smith reagents.

* * * * *